(12) United States Patent
Hartlep et al.

(10) Patent No.: US 8,702,580 B2
(45) Date of Patent: Apr. 22, 2014

(54) METHOD AND DEVICE FOR ASSISTING IN A TISSUE TREATMENT

(75) Inventors: Andreas Hartlep, München (DE); Christoph Pedain, München (DE)

(73) Assignee: Brainlab AG, Feldkirchen (DE)

( * ) Notice: Subject to any disclaimer, the term of this patent is extended or adjusted under 35 U.S.C. 154(b) by 1682 days.

(21) Appl. No.: 11/244,867

(22) Filed: Oct. 6, 2005

(65) Prior Publication Data

US 2006/0085175 A1  Apr. 20, 2006

Related U.S. Application Data

(60) Provisional application No. 60/618,854, filed on Oct. 14, 2004.

(30) Foreign Application Priority Data

Oct. 6, 2004  (EP) .................................... 04023784

(51) Int. Cl.
*A61M 3/00* (2006.01)
(52) U.S. Cl.
USPC ............................................... 600/4; 600/431
(58) Field of Classification Search
USPC .................. 600/1–8, 431, 424, 429, 433, 436
See application file for complete search history.

(56) References Cited

U.S. PATENT DOCUMENTS

| | | | |
|---|---|---|---|
| 5,302,369 A * | 4/1994 | Day et al. | 424/1.29 |
| 5,735,814 A | 4/1998 | Elsberry et al. | |
| 6,011,563 A | 1/2000 | Fournier et al. | |
| 6,026,316 A | 2/2000 | Kucharczyk et al. | |
| 6,095,975 A | 8/2000 | Silvern | |

(Continued)

OTHER PUBLICATIONS

European Search Report for corresponding Application No. 04023784 dated Apr. 13, 2005.

(Continued)

*Primary Examiner* — Charles A Marmor, II
*Assistant Examiner* — Carrie R Dorna
(74) *Attorney, Agent, or Firm* — Tucker Ellis LLP

(57) ABSTRACT

A method for planning to treat tissue by administering a substance which emits energy or can interact with administered energy to a body, such as body tissue, wherein a dispersion of the substance in the body is simulated, and to a system or device for planning administering a substance and administering energy to a body or in body tissue. The device includes a data capture unit configured to detect patient-specific parameters, wherein the patient-specific parameters can be used to describe a dispersion behavior of the substance in the body or body tissue; a computational unit operatively coupled to the data capture unit, said computational unit configured to obtain the patient-specific parameters from the data capture unit; a database accessible by the computational unit, wherein the database includes data for describing characteristics of a particular type of tissue or a particular body structure, data for describing mechanisms for supplying energy, and/or data for describing the effect on tissue of a substance in combination with supplied energy, the computational unit being configured to retrieve and/or store said data in the database; and an input unit via which a user can input treatment-specific data to the computational unit, wherein the computational unit is configured to simulate the plan based on at least one of the patient-specific data, data stored in the database, or user input data.

13 Claims, 2 Drawing Sheets

(56) References Cited

U.S. PATENT DOCUMENTS

| | | |
|---|---|---|
| 6,746,661 B2 | 6/2004 | Kaplan |
| 2001/0044567 A1* | 11/2001 | Zamora et al. ............... 600/3 |
| 2003/0088146 A1* | 5/2003 | Slater et al. ............... 600/8 |
| 2003/0112922 A1* | 6/2003 | Burdette et al. ............... 378/65 |
| 2003/0114751 A1 | 6/2003 | Pedain et al. |
| 2003/0175356 A1* | 9/2003 | Faisant et al. ............... 424/490 |

OTHER PUBLICATIONS

European Search Report for corresponding Application No. 04023784 dated May 30, 2005.

Hamacher K.A. et al.; "Theoretical estimation of absorbed dose to organs in radioimmunotherapy using radionuclides with multiple unstable daughters"; Medical Physics, American Institute of Physics; New York, NY; Sep. 2001; pp. 1857-1874; XP012011572.

Furhang E.E. et al.; "A Monte Carlo Approach to Patient-Specific Dosimetry"; Medical Physics, American Institute of Physics; New York, NY; Sep. 1996; pp. 1523-1529; XP000640764.

Ahmad S.U. et al.; "A New Recursive Algorithm for Optimization in Intensity Modulated Radiotherapy"; Engineering in Medicine and Biology Society, 2000; Proceedings of the $22^{nd}$ Annual International Conference of the IEEE, Jul. 23-28, 2000; pp. 3100-3103; EP010531299.

* cited by examiner

METHOD AND DEVICE FOR ASSISTING IN A TISSUE TREATMENT

RELATED APPLICATION DATA

This application claims priority of U.S. Provisional Application No. 60/618,854 filed on Oct. 14, 2004, which is incorporated herein by reference in its entirety.

FIELD OF THE INVENTION

The present invention relates to a method and device for tissue treatment and, more particularly, to improving the combined treatment of tissue by administering a substance or a combination of substances.

BACKGROUND OF THE INVENTION

When treating tissue such as tumors in the brain, the prostate, the trunk of the body, the liver, the chest, etc., a solid, liquid or gaseous substance, such as a radioactive substance, for example, can be delivered into the tissue or into the vicinity of the tissue, to perform so-called near-field irradiation on the infected tissue. The introduced radioactive solids, liquids or gases which, for example, emit beta radiation, can destroy the tumor.

As an alternative to these brachytherapy methods wherein tissue is irradiated using a radioactive substance introduced into or in the vicinity of the tissue to be irradiated, a radiotherapeutic or radiosurgical method also can be performed. In radiotherapeutic or radiosurgical methods, for example, the tissue can be irradiated using a radiation source guided or positioned around the body. In this case, substances (so-called sensitizers) are often introduced into the body, in particular into the area of the tissue to be treated. The substances, for example, can make tumor cells more sensitive to radioactive or light beams or also to the effect of heat. In treating a tumor, high doses of said sensitizers and high radiation doses generally are used in order to kill the bulk of the tumor cells. However, administering a high dose of sensitizers or irradiating body tissue with a high dose of radioactive radiation can also have undesirable effects on healthy tissue that is not to be treated.

Infusing medicines into the brain to treat neurodegenerative dysfunctions by means of an implantable pump and a catheter is known from U.S. Pat. No. 5,735,814, wherein the stimulus levels of the neurons in the brain are altered by means of the administered substances.

U.S. Pat. No. 6,026,316 describes monitoring the administration of a substance by means of nuclear spin tomography.

A solid substance which can be used in brachytherapy and which can be implanted is known from U.S. Pat. No. 6,746,661 B2.

SUMMARY OF THE INVENTION

A method is provided that simulates and/or plans administration of a substance such as a sensitizer (e.g., a radiosensitizer, photosensitizer, thermosensitizer or the like) or, for example, in combination with administering a desensitizer at another point in the body. The desensitizer can be administered by simulating the dispersion of the substance in the body based on the administration or infusion parameters of the substance and/or substance-specific parameters.

In addition, it is possible to calculate, based on the simulated dispersion of the substance in the body, the energy that should be supplied to the body, the form of the energy and/or delivery of the energy, in order for the administered substance and the energy supplied to the body or tissue to generate a desired effect on the tissue (e.g., targeted destruction of tumor cells). A user can be assisted in optimizing the treatment on the basis of displayed simulation results or partial results, such that the desired effect occurs with an increased probability.

The substance or substances and/or active agents (hereinafter substance) that are administered at one or more points on a body, for example by infusion, can be a liquid or also solid substance that does not dissolve until in the body, interaction with a bodily liquid, or interaction with a supplied liquid. The substance can contain radioactive elements that can interact with other administered substances or fluids, for example, in order to enable a particular and predetermined area or type of tissue to be treated or destroyed using targeted destruction.

With respect to a method for planning an infusion in accordance with one embodiment, and in particular with respect to using patient data for planning or performing the infusion, reference is made to the teaching of EP 1 316 324 A1 belonging to the Applicant, which is incorporated herein by reference in its entirety. Using patient data or patient parameters obtained via imaging techniques such that, for example, one or more suitable catheters can be selected for infusion from a predetermined set of catheters, together with one or more points, and positioned using one or more of said data with regard to the insertion location and/or depth of penetration, is particularly advantageous for planning the infusion. Patient data or patient parameters can be obtained, for example, via known nuclear spin resonance (MRI) methods, computer tomography (CT) methods, x-ray methods, ultrasound methods or other methods that enable the spatial structure of a body and in particular the tissue structure or tissue characteristics to be detected and displayed and/or functional data such as, for example, patient-specific diffusion or perfusion characteristics or parameters to be obtained. Equally, a suitable infusion agent can be advantageously selected, or the composition of an infusion agent specified and, for example, the course over time of the dispensing pressure or the duration of administering the substance can be calculated on the basis of one or more of said data.

If the dispersion in the body of the substance has been simulated, in particular taking into account body-specific data or general action mechanisms that influence the dispersion of a substance in the body (e.g., the blood-brain barrier or the metabolism), then it is possible to establish the parts of the body where energy should be provided or supplied. The amount or concentration of the one or more administered substances also can be ascertained by simulation. In addition, it is possible to calculate, based on the simulation results or partial results, what effect the energy applied to the tissue will have. In particular, based on the simulated dispersion of the substance(s) in the body or tissue, it is possible to calculate a distribution of the energy to be administered in order to achieve, in combination with the administered substance situated in the body, an optimal effect. For example, it is possible to calculate the point or area of the body or tissue that should be irradiated, such that in conjunction with the radiosensitizer utilized at the same point or area (at a particular concentration), a precise effect can be created on a particular area of tissue or particular types of cell. Furthermore, additional irradiation parameters can be calculated, such as, for example, positioning or guiding a radiation source that can be introduced into the body or can be arranged outside the body and guided around the body. It is equally possible to not supply energy or to supply energy in the form of ionizing radiation, as heat energy, and/or light energy, in order to interact with an administered substance. Furthermore, supplying cooling energy in the form of a cold or cooling substance or liquid, for example, in a targeted or directed way can be understood as supplying energy, which in conjunction with a substance introduced into a tissue can generate an effect on tissue and, in particular, destroy a particular type of cell.

Body or tissue characteristics, such as, for example, general or individual-specific characteristics of the brain, can be ascertained using MRI, ultrasound, CT, PET, SPECT, biopsy or other known measuring methods. In such methods, body or tissue characteristics may be understood as characteristics that are relevant to the dispersion or chemical composition of one or more administered substances, such as, for example, diffusion or perfusion characteristics, the effect of the metabolism, or the spatial formation of one or more tissue structures.

Preferably, the effect of the administered substance on the tissue is taken into account in the simulation of the dispersion of the substance in the body or tissue, such as, for example, a change in the tissue density, a change in the proportion of extracellular space in the overall volume of a part of the tissue, and the sensitivity of the tissue to heat or a radiation dose, in order to kill a particular type of cell and to realistically simulate or take into account the absorption behavior or interaction with the administered energy. Furthermore, it is possible to simulate the therapeutic effect of administering one or more substances in combination with supplying energy, in order to assess the effect of treating the tissue, as a simulation result.

The simulation method also can be used iteratively. For example, a first planning step (proceeding from an initial data set, for example an initial position of a catheter and an initial dose of a substance to be administered) calculates or simulates whether a desired treatment result occurs, and proceeding from the simulation result, modifies the treatment plan in order to achieve a possibly improved treatment result. The simulation can be performed in conjunction with a predetermined energy amount inserted or applied at one or more particular points once the substance has been administered as described above. The method can be iterated in this way until an optimum treatment result or, for example, a treatment result above a predetermined limit (e.g., the destruction of at least 80% of the cells of a tumor) is achieved.

Furthermore, the parameter or data set ascertained using the method for planning the administration of a substance and energy as described above can be relayed or communicated to a known navigation system in order to perform the planned method. When performing the method, it is also possible to monitor the progression of the treatment using a nuclear spin resonance method, as for example described in U.S. Pat. No. 6,026,316, the contents of which is hereby incorporated by reference in its entirety, and for example to verify whether the actual course of treatment matches the planned treatment. If there is a deviation, infusion parameters or the amount of energy administered can be altered and, for example, further planning and/or simulations can be performed using the altered parameters to achieve a desired treatment result. Once the substance has been administered, in combination with supplying energy, the result of the treatment can be examined and deviations from the calculated or simulated result can be used to modify a simulation in a subsequent treatment.

In accordance with another aspect of the invention, there is provided a simulation method for determining the effects of treating a tissue by introducing a substance and supplying energy to the substance and/or tissue, in order to ascertain what effect the combined application of the substance and the supplied energy has on the treated tissue.

The invention further provides a computer program which, when it is loaded onto a computer or is running on a computer, performs a method as described above. Equally, the invention relates to a program storage medium or a computer program product comprising such a program.

A system or device for planning the administration a substance may include a data input device that, for example, can be connected to a data capture unit such as a nuclear spin tomograph or computer tomograph, for example, or is such a unit. The input data can be supplied to a computational unit or computer that can evaluate the input data, such as, for example, image data, and which also obtains anatomical data from a database, for example, with respect to the metabolic characteristics or electrical conductivity of the tissue to be treated. The computational unit can include a conventional computer, a neural network and/or a fuzzy logic, in order to ascertain patient-specific parameters such as, for example, the electric or thermal conductivity of the tissue or a pressure distribution in the tissue. The patient specific parameters can be ascertained from a data set such as, for example, measurement results from a data capture unit for individually examining a body or tissue structure. The computational unit also can simulate the dispersion of the substance, such as the dispersion of a fluid, the concentration of a fluid and/or the distribution of energy, using the patient-specific ascertained information. In addition, general biological or anatomical functions can be adduced from the database in which a generic model is stored, for example.

The system or device preferably includes a navigation system and/or a monitoring unit from which the execution and/or result of the treatment can be verified. If the actual course of treatment deviates from the planned or simulated course of treatment, one or more treatment parameters, such as infusion or irradiation parameters, for example, can be modified.

The invention further provides and apparatus and method for using a radioactive liquid as an agent for treating a tissue (brachytherapy seed) to enable greater specificity, as opposed to using solid substances introduced into the body. The invention also provides enhanced precision for treatment and/or irradiation of a predetermined target volume. In particular, the radioactive liquid can be introduced or dispersed as above or as described in EP 1 316 324 A1 belonging to the Applicant, or by filling a balloon or balloon-tipped catheter.

DETAILED DESCRIPTION

Figure 1:
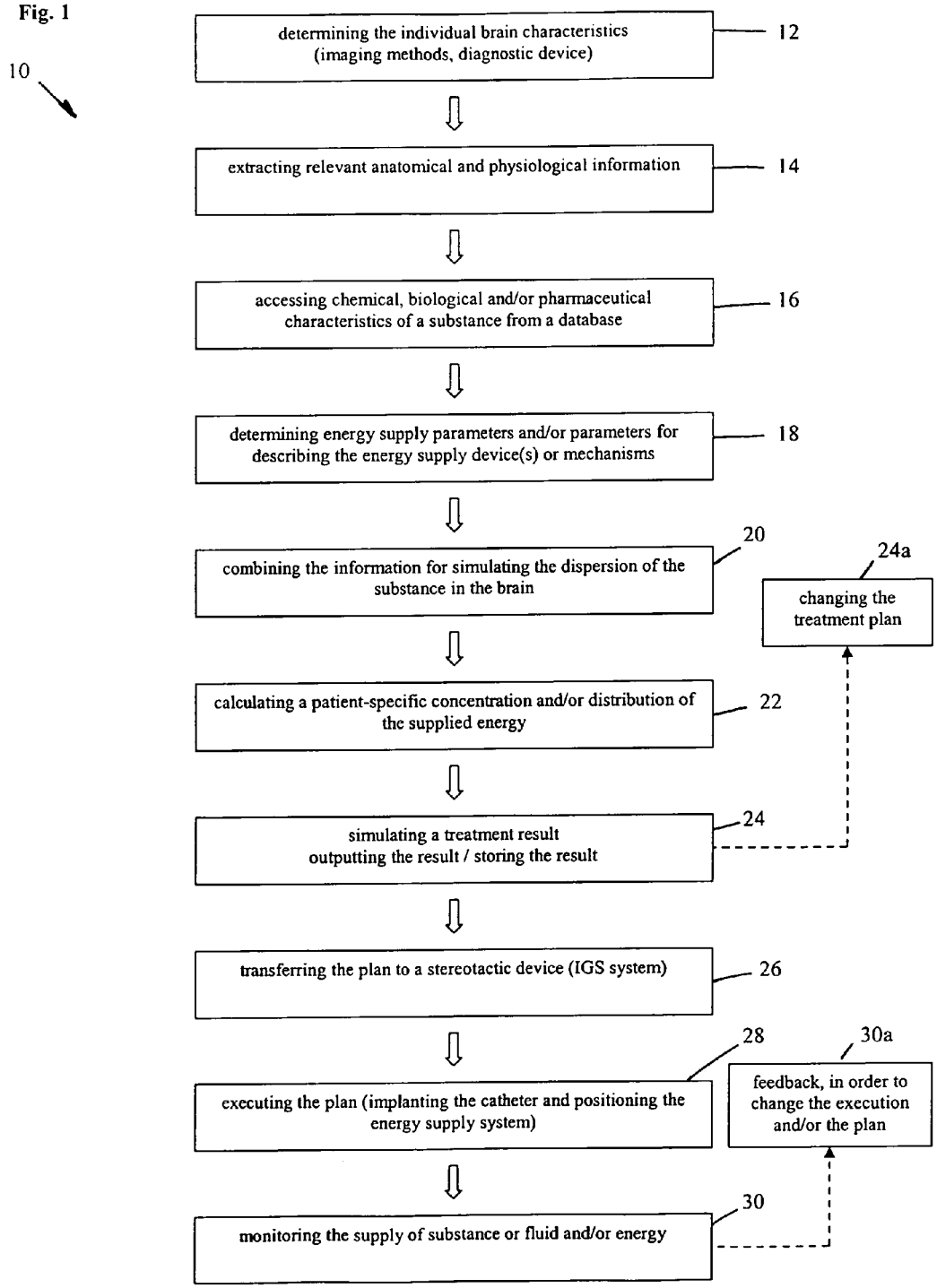
FIG. 1 a flow diagram of a method for tissue treatment in accordance with an embodiment of the invention.

FIG. 1 illustrates a flow chart 10 in accordance with an embodiment for treating a brain tumor. As will be appreciated, the invention can be used to treat numerous regions of the body, and the context of treating a brain tumor is not intended to be limiting.

The flow diagram includes a number of process blocks arranged in a particular order. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

Beginning at step 12, the individual brain characteristics or brain parameters of the patient are determined using, for example, known imaging methods can be used, such as nuclear spin tomography, ultrasound, computer tomography, PET, SPECT, biopsy or other known methods. The captured data for describing characteristics of the brain are then evaluated at step 14 to obtain relevant anatomical, physiological and/or functional information. To this end, a generic model can be used, or known mathematical models can be used for ascertaining specific characteristics (e.g., characteristics relevant to the dispersion of a substance or to the absorption of energy) from the captured data. In particular, the thermal diffusibility, course of nerve tracts, density distribution, elasticity, liquid content, blood content, blood flow values, vascular permeability or other information for describing characteristics or structures of the brain can be used. If, for example, patterns known from a generic model or general information are used, then characteristics of the brain can be estimated for particular volumes or areas of the brain, if they have not been ascertained directly by measurement.

The information ascertained by measurement and/or a generic model, or from a database, which may be relevant to the method in accordance with the invention, can be one or more of the following mechanisms or characteristics:

transport mechanism in the body (for example for bodily liquids or externally administered liquids or substances);

discharge or dispersion of a liquid in the body or tissue (dependent inter alia on the permeability or on physiological characteristics, such as for example the blood-brain barrier);

hydraulic and/or chemical and/or biological characteristics at body structure boundaries (blood-brain barrier, sulci);

diffusion which has an effect on the transport mechanism of a substance in the tissue;

conductivity;

degree of energy sensitivity;

degree of energy absorption;

anatomical information (white/grey substance).

If, using one or more of the above characteristics or mechanisms, a model of the region (e.g., a brain or body region) to be treated has been produced that describes the transport or dispersion of a substance or liquid introduced into the region or is situated in the region, then the dispersion in the region of a liquid introduced into the region to be treated can be simulated to obtain a local dispersion and/or dose. In other words, the absolute amount or concentration of a particular substance situated in a particular region or a particular structure of the tissue can be ascertained, such as in a particular area of the brain or body, for example.

At step 16, general chemical, biological and/or pharmaceutical characteristics of the administered substance can be obtained from a database, for example. These characteristics can be used to carry out the simulation, wherein one or more of the following types of information or characteristics can be adduced in order to simulate the dispersion of the liquid or substance:

information with respect to the administration parameters of the substance (such as for example local administration in tissue or systemic administration, the duration of administration or infusion, the effect of the metabolism (metabolization) on the active substance or the carrier mechanism or carrier substance, the arrangement of the supply devices such as, for example, the catheter and pumps);

measured or assigned and/or determined characteristics of the target area or tissue;

pharmaceutical characteristics of the respective agent (such as, for example, heat-sensitive liposomes, energy or particle-emitting liquids, radiation sensitizers, toxins, etc.);

mathematical model that uses the aforementioned information, and using which a dispersion of the liquid and/or a dose can be calculated.

At step 18, parameters regarding the energy supply and information with respect to the device or mechanisms by which the energy is supplied are used to simulate the supply of radiation energy, light energy or heat energy, for example, in tissue. To simulate the supply of energy, one or more of the following types of information can be used:

measured or assigned characteristics of the target area;

information regarding the arrangement or concentration of substances, objects or liquids which have an effect on the energy sensitivity parameters and/or absorption parameters of the target area;

positional information on the energy-emitting objects or liquids;

emission characteristics of the objects or liquids;

time parameters regarding the arrangement or dispersion of the objects or liquids;

energy administering parameters from sources arranged outside the target area;

a mathematical model that uses the information above and can determine a local dispersion of the energy supply.

At step 20, the simulation results described above are combined. In other words, the effect the simulated administration of energy (e.g., in accordance with a treatment plan for supplying energy in different doses) has in various regions or areas of the body is ascertained, taking into account the simulated dispersion of one or more substances or liquids in a tissue or body structure. It is then possible to determine whether tumor cells, for example, can be destroyed in sufficient amounts using the treatment plan data used for the simulation. The data can include, for example, the location of a catheter for introducing a substance and a characteristic dispensing curve of the substance. The characteristic dispensing curve can describe the course over time of an amount of substance that is dispensed, or pressure at which the substance is introduced into the tissue. Further, the mechanisms for supplying energy described in step 18 also can be taken into account.

The calculated patient-specific concentration of the introduced substance, the dispersion of the substance or liquid, and/or the distribution of energy are calculated at step 22. At step 24, the treatment plan is simulated and the results are output (e.g., on a video display) and stored (e.g., in computer memory).

It is possible to simulate the reaction of the target area over time, wherein the parameters for describing tissue behaviour can be altered over time to describe the dynamic behaviour of the target area. For example, effects on the tissue arising from the treatment (e.g., from the administered substance or the supplied energy) can be taken into account in planning the treatment.

A data set ascertained by a computational unit using the method described above can be output, for example graphically, in order to display one or more of the following types of information:

dispersion of the substances and/or carrier substances of the substances or medicines;

locally varying concentration of the substances and/or carrier substances;

distribution of energy in the tissue in the case of energy-emitting substances;

distribution of energy of an external energy source;

distribution of energy, taking into account the effect of the administered liquids or substances that alter the energy absorption and/or energy sensitivity of the target area (effect distribution).

If, after simulating, it is established that a desired or predetermined treatment result is not achieved or not completely achieved, then the method can be performed iteratively. More specifically, treatment parameters, such as the dosing or the administration mechanisms of the externally supplied substances or liquids, or the mechanisms for supplying energy, are altered and a new simulation is performed using the altered initial parameters until a satisfactory simulation result is obtained, as indicated at step 24*a*.

If the simulation result is satisfactory, then at step 26 the treatment plan can be transferred to a stereotactic device such as, for example, an image-guided surgery (IGS) system. At step 28, the IGS can execute the treatment plan so as to position a catheter or catheters at the points ascertained by the simulation as being favorable, for example.

At step 30, the supply of the liquid or substance and/or energy can be measured or monitored while the treatment is performed to provide the user feedback as to whether the treatment plan is being performed correctly or should be changed. At step 30*a*, adjustments to the parameters for supplying the substance or a liquid or for supplying energy can be made to obtain an improved treatment result, for example.

Figure 2:
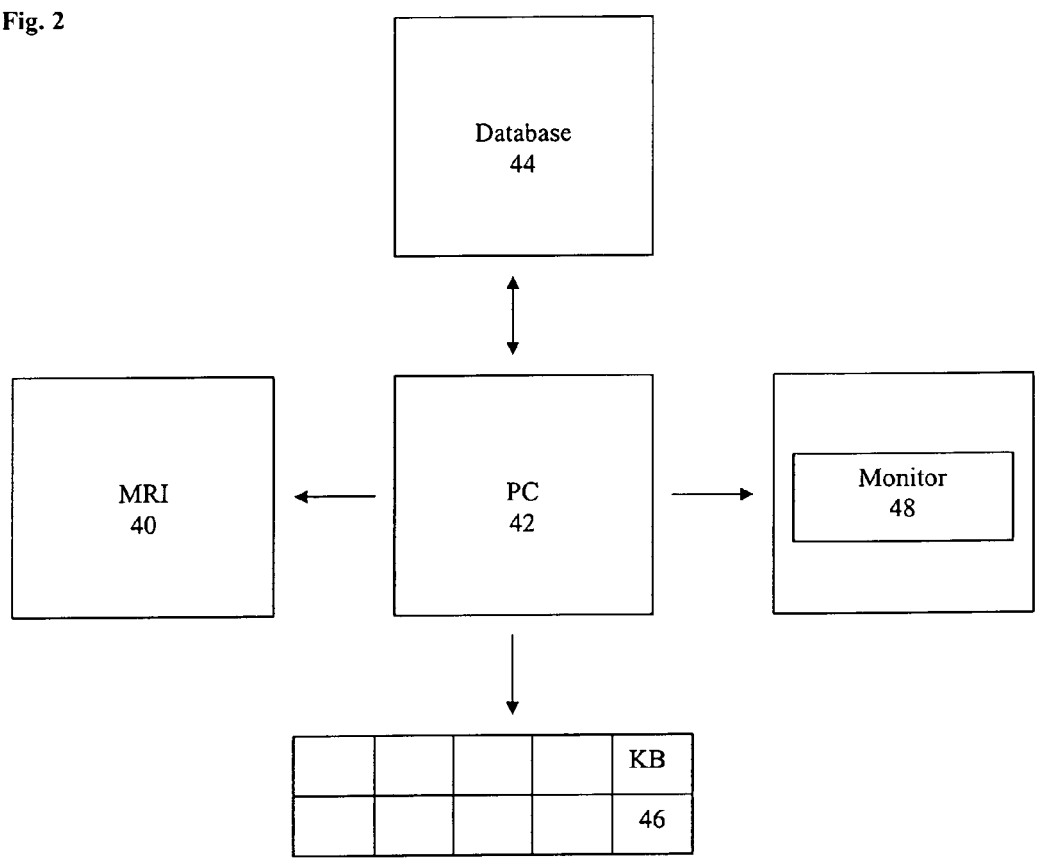
FIG. 2 is a schematic diagram of a system or device for assisting in tissue treatment in accordance an embodiment of the invention.

FIG. 2 shows an embodiment of the system or device in accordance with the invention, wherein a nuclear spin resonance tomograph 40 captures patient-specific data and outputs the data to a computational unit 42 The computational unit 42 is connected to a database 44 in which a generic model of the area of the body detected by the nuclear spin tomograph 40 is stored. The computational unit 42 forms a model of the body structure from the data transmitted from the nuclear spin tomograph 40 and the database 44, the model describing the patient-specific characteristics regarding the dispersion of a substance supplied to the body structure.

Further data with respect to the type of a substance to be administered or the type of the energy supplied, for example, can be input to the computational unit 42 by a user via an input unit such as a keyboard 46 or the like. To this end, the computational unit 42 can access additional information from the database 44, for example, with respect to the physical, chemical or physiological characteristics of the substance, in order to perform the method described above. The simulation results ascertained by the computational unit 42 can be displayed graphically on a monitor 48.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for planning to treat tissue by administering a substance to a body or body tissue, comprising:
   using a processor to simulate a dispersion of the substance in the body or body tissue, said dispersion corresponding to movement of the substance through the body or body tissue, wherein said substance comprises a substance that emits energy or interacts with administered energy;
   simulating a therapeutic effect that supplying at least one of external radiation energy, heat energy, cooling energy or light energy has on at least one of the administered substance, the body or body tissue, wherein simulating the therapeutic effect takes into account the simulated dispersion of the substance in the body or body tissue; and
   iteratively performing the simulation when a result of the simulation indicates the effect on the body or body tissue is below a predetermined minimum effect.

2. The method as set forth in claim 1, further comprising simulating the interaction of the substance with the body or body tissue.

3. The method as set forth in claim 1, further comprising ascertaining and using in the simulation body or body tissue characteristics of one or more types of body tissue.

4. The method of claim 3, wherein ascertaining and using body or body tissue characteristics includes physical, chemical or physiological parameters of the body or body tissue.

5. The method according to claim 1, further comprising:
   simulating at least one of an effect that the body or body tissue, the administration of the substance, or the delivered energy has on the substance.

6. The method as set forth in claim 1, further comprising transferring one or more parameters used in the simulation to a navigation system, wherein said parameters describe at least one of administration of the substance or administration of energy, and wherein the navigation system executes the treatment when a result of the simulation achieves a predetermined result.

7. The method as set forth in claim 1, further comprising:
   examining an effect of at least one of administering the substance or administering the energy; and
   re-planning the treatment if actual treatment deviates from the simulated treatment.

8. The method as set forth in claim 1, further comprising using a radioactive liquid as an agent for brachytherapy.

9. A computer program embodied on a non-transitory computer readable storage medium, wherein the program instructs a processor to perform the method as set forth in claim 1.

10. The method according to claim 1, wherein the substance is a substance that emits energy, further comprising calculating a distribution of the energy emitted by the substance.

11. The method according to claim 1, wherein the substance is a sensitizer.

12. The method according to claim 1, further comprising:
   determining anatomical or physiological information concerning the body or body tissue;
   determining characteristics of the substance;
   determining energy supply parameters; and using the determined anatomical or physiological information, characteristics of the substance, and energy supply parameters to perform the simulation.

13. The method according to claim 1, further comprising:

based on the simulated dispersion of the substance in the body or body tissue, simulating a distribution of energy supplied by the substance or by an energy source to the body or body tissue; and simulating an effect of administering the substance and supplying the energy has on the body or body tissue.

* * * * *